US 10,486,189 B2

(12) United States Patent
Hiemer et al.

(10) Patent No.: US 10,486,189 B2
(45) Date of Patent: Nov. 26, 2019

(54) APPLICATOR FOR EJECTING DOSES OF A FLOWABLE COMPONENT

(71) Applicant: Sulzer Mixpac AG, Haag (CH)

(72) Inventors: Andreas Hiemer, Rebstein (CH); Michaela Noack, Lustenau (AT)

(73) Assignee: SULZER MIXPAC AG, Haag (CH)

( * ) Notice: Subject to any disclaimer, the term of this patent is extended or adjusted under 35 U.S.C. 154(b) by 35 days.

(21) Appl. No.: 15/762,753

(22) PCT Filed: Sep. 26, 2016

(86) PCT No.: PCT/EP2016/072879
§ 371 (c)(1),
(2) Date: Mar. 23, 2018

(87) PCT Pub. No.: WO2017/051039
PCT Pub. Date: Mar. 30, 2017

(65) Prior Publication Data
US 2018/0264507 A1 Sep. 20, 2018

(30) Foreign Application Priority Data
Sep. 25, 2015 (EP) ..................................... 15186916

(51) Int. Cl.
*B05C 17/005* (2006.01)
*A61B 17/00* (2006.01)
(Continued)

(52) U.S. Cl.
CPC .. *B05C 17/00586* (2013.01); *A61B 17/00491* (2013.01); *A61M 35/003* (2013.01);
(Continued)

(58) Field of Classification Search
CPC ......... B67B 7/24; B67B 7/26; B65D 83/0033; B65D 83/0005; B05C 17/00586;
(Continued)

(56) References Cited

U.S. PATENT DOCUMENTS 2,022,706 A * 12/1935 Clark ...................... F16N 37/02
206/384
2,102,591 A * 12/1937 Hagemeier ............. A61M 5/24
222/386
(Continued)

FOREIGN PATENT DOCUMENTS

EP 1188455 A1 3/2002
EP 0982078 B1 10/2003
(Continued)

OTHER PUBLICATIONS

International Preliminary Report on Patentability and Written Opinion dated Mar. 27, 2018 in corresponding International Application No. PCT/EP2016/072879, filed Sep. 26, 2016.
(Continued)

*Primary Examiner* — Patrick M. Buechner
(74) *Attorney, Agent, or Firm* — Global IP Counselors, LLP

(57) ABSTRACT

An applicator for ejecting doses of a flowable component includes a housing, an application tip connected to the housing, an actuation mechanism, and an insert which is detachable from the housing. The insert is adapted to be inserted into the housing, and has a storage volume for the flowable component. The housing includes a receiving portion adapted to the insert. The insert includes a drive portion which is adapted to cooperate with the actuation mechanism so that the operation of the actuation mechanism results in a displacement of the insert relative to the housing and on a displacement axis.

20 Claims, 3 Drawing Sheets

(51) Int. Cl.
  *G01F 11/02* (2006.01)
  *A61M 35/00* (2006.01)
  *B05C 17/01* (2006.01)

(52) U.S. Cl.
  CPC .... *B05C 17/00596* (2013.01); *B05C 17/0116* (2013.01); *G01F 11/027* (2013.01); *A61M 2210/04* (2013.01)

(58) Field of Classification Search
  CPC ........ B05C 17/00593; B05C 17/00596; B05C 17/012; B05C 17/0123; B05C 17/0126; B05C 17/0116; G01F 11/026; G01F 11/027; G01F 11/025; A61B 2017/00407; A61M 35/003; A61M 35/006
  See application file for complete search history.

(56) References Cited

U.S. PATENT DOCUMENTS

| | | | | |
|---|---|---|---|---|
| 2,373,774 | A * | 4/1945 | Murnane | B05C 17/00516 222/326 |
| 3,161,325 | A * | 12/1964 | Hinkel | A47G 19/34 222/327 |
| 3,924,623 | A * | 12/1975 | Avery | A61M 35/006 604/3 |
| 4,065,036 | A * | 12/1977 | Kirk, Jr. | B05B 11/3059 222/153.13 |
| 4,355,736 | A * | 10/1982 | Schumacker | B65D 83/64 222/386.5 |
| 4,507,111 | A * | 3/1985 | Gordon | A47K 7/028 401/134 |
| 4,744,494 | A * | 5/1988 | Seager | B05C 17/0123 16/225 |
| 4,747,719 | A * | 5/1988 | Parkin | A61M 35/006 401/132 |
| 4,941,873 | A * | 7/1990 | Fischer | A61M 3/00 604/500 |
| 5,042,690 | A * | 8/1991 | O'Meara | A45D 34/042 206/15.2 |
| 5,310,091 | A | 5/1994 | Dunning | |
| 5,324,305 | A * | 6/1994 | Kanner | A61B 17/00491 222/146.2 |
| 5,427,280 | A | 6/1995 | Fuchs | |
| 5,490,736 | A * | 2/1996 | Haber | A61M 35/006 401/132 |
| 5,735,437 | A | 4/1998 | Broyles et al. | |
| 7,448,868 | B2 | 11/2008 | Delval et al. | |
| 8,807,859 | B2 | 8/2014 | Stenton | |
| 8,851,336 | B2 | 10/2014 | Weill et al. | |
| 9,067,024 | B2 | 6/2015 | Roberts et al. | |
| 2004/0102741 | A1 * | 5/2004 | Paulhus | A61M 35/003 604/290 |
| 2006/0264838 | A1 | 11/2006 | Volckmann et al. | |
| 2008/0227052 | A1 * | 9/2008 | Peuker | B05C 17/00553 433/89 |
| 2009/0224004 | A1 * | 9/2009 | Muller | B05C 17/01 222/309 |
| 2010/0105003 | A1 | 4/2010 | Weill et al. | |
| 2011/0030191 | A1 | 2/2011 | Weill et al. | |
| 2011/0066121 | A1 * | 3/2011 | Hoang | A45D 34/04 604/310 |
| 2011/0270197 | A1 | 11/2011 | Weill et al. | |
| 2012/0248152 | A1 | 10/2012 | Weill et al. | |
| 2013/0204196 | A1 | 8/2013 | Roberts et al. | |
| 2017/0348517 | A1 * | 12/2017 | Colombo | A61M 35/003 |

FOREIGN PATENT DOCUMENTS

| | | |
|---|---|---|
| EP | 2269517 A1 | 1/2011 |
| EP | 2034903 B1 | 10/2012 |
| WO | 9917833 A1 | 4/1999 |
| WO | 2005084819 A2 | 9/2005 |
| WO | 2008064283 A2 | 5/2008 |
| WO | 2014086559 A1 | 6/2014 |
| WO | 2014086635 A1 | 6/2014 |
| WO | 2015003762 A1 | 1/2015 |

OTHER PUBLICATIONS

International Search Report dated Dec. 16, 2016 in corresponding International Application No. PCT/EP2016/072879, filed Sep. 26, 2016.

Extended European Search Report dated Mar. 16, 2016 in corresponding European Patent Application No. 15186916.1, filed Sep. 25, 2016.

* cited by examiner

APPLICATOR FOR EJECTING DOSES OF A FLOWABLE COMPONENT

CROSS-REFERENCE TO RELATED APPLICATION

This application is a U.S. National Stage application of International Application No. PCT/EP2016/072879, filed Sep. 26, 2016, which claims priority to European Application No. 15186916.1, filed Sep. 25, 2015, the contents of each of which are hereby incorporated herein by reference.

BACKGROUND

Field of the Invention

The present invention relates to an applicator for ejecting doses of a flowable component, the applicator comprising a housing, an application tip connected to the housing, an actuation mechanism and an insert which is detachable from the housing, the insert being adapted to be inserted into the housing, the insert having a storage volume for the flowable component. The housing comprises a receiving portion adapted to the insert.

Background of the Invention

Applicators are known in the prior art that permit the dispensing of flowable components, such as adhesives or other substances. The substances can, for example, be used in medical applications for wound care or in DIY applications for sealing and/or bonding purposes. Common to at least these two types of applications is the use of cyanoacrylate (CA). CA is a fast setting adhesive particularly when it is in contact with water. Humidity in air can also cause the CA to set. For this reason CA has to be stored in a sealed air-tight container.

Some applications therefore use glass ampules as a storage container. Glass ampules provide an air-tight seal. However, in use a part of the glass ampule is broken off, such that the possibility exists that miniscule glass splinters remain in the CA, which would also be dispensed at the position of application of the CA. This should in particular be avoided with regard to medical applications.

Moreover, targeted dispensing from a glass ampule is not generally possible via the that is broken off. Other applications use plastic applicators in which the CA is sealed in a compartment. Particularly, the CA can be stored in an insert for the applicator. The applicator then provides an ejection mechanism, e.g. a plunger that is adapted to move a piston of the insert. When moved, the piston of the insert reduces the storage volume and thereby ejects the CA.

SUMMARY

The handling of such applicators can be laborious since prior to inserting the insert, the plunger has to be brought into a retracted position. After the insertion of the insert, the plunger has to be adapted to the position of the insert, i.e. the plunger has to be brought in a starting position. In the retracted position and the starting position the plunger often stands out from the housing of the applicator, thus, further impairing an easy handling of the applicator.

In view of the foregoing it is an object of the present invention to provide an applicator which allows easy handling and at the same time can be manufactured in an economic manner. It is a further object of the invention to provide an applicator which allows ejecting doses of a constant volume.

These objects are achieved by an applicator having the features described herein.

Particularly, these objects are satisfied by an applicator having an insert which comprises a drive portion which is adapted to cooperate with the actuation mechanism so that the operation of the actuation mechanism results in displacement of the insert relative to the housing along a displacement axis.

The invention is based on the finding that the handling of an applicator can be improved if the insert itself is moved relative to the housing in order to eject or dispense the flowable component. Particularly, the insert can be moved in its entirety.

The applicator therefore does not require a plunger or a drive mechanism which is substantially completely arranged at the housing of the applicator. Rather, the insert comprises parts of such a drive mechanism, namely the drive portion. Thereby the need to operate or to move the drive mechanism before inserting the insert into the housing is eliminated. Since the insert comprises parts of the drive mechanism, i.e. the drive portion, by inserting the insert into the receiving portion of the housing the drive portion is automatically set up for operation.

In other words, the steps required by applicators of the prior art, namely (1) moving the drive mechanism into a retracted position, (2) inserting the insert into the housing and (3) moving the drive mechanism into a starting position are no longer necessary. Instead, the insert only has to be placed in the housing. After this single step of preparation of the applicator, the applicator can then be ready for use. The inventive applicator thus dramatically reduces the handling effort for its operation.

Further, the actuation mechanism can be advantageously arranged at the housing, whereas the drive portion is arranged at the insert. This separated drive mechanism can be manufactured in a simple and economic process, thereby reducing the costs for the production of the applicator.

It is to be noted that the term "arranged at" includes "adjacent to", "comprises" and "directly connected to". As an example, the actuation mechanism can either be directly connected to the housing (and preferably be integral with the housing) or be arranged adjacent to the housing. The housing may also comprise the actuation mechanism.

After the insert is received in the receiving portion of the housing, the actuation mechanism can be operated, whereby the actuation mechanism cooperates with the drive portion. This cooperation leads to a displacement of the insert relative to the housing along the displacement axis. The displacement of the insert can eject a dose of the flowable component through the application tip. Subsequent operations of the actuation mechanism displace or move the insert incrementally along the displacement axis. The incremental movements can have the same step width.

The displacement axis can form the center of the applicator, i.e. the applicator can be substantially symmetrical with respect to the displacement axis.

Preferably the applicator is configured such that at least two subsequent operations of the actuation mechanism result in displacement of the insert relative to the housing along the displacement axis. A stepwise application or ejection of the flowable component is therefore possible. Advantageously a plurality of subsequent operations of the actuation mechanism can be performed, wherein each operation substantially ejects the same volume of flowable component. It is thus possible to eject the flowable component in small doses. Hence, the applicator can be used in applications that require very small doses or a repeatable ejection of a component.

Advantageously the actuation mechanism and the drive portion are configured to allow and/or effect only a displacement of the insert in one direction along the displacement axis. The displacement can only be effected in the direction toward the application tip. A backwards movement can be blocked. Thereby air or humidity can be prohibited or prevented from being sucked into the storage volume. Air or humidity could deteriorate the flowable component stored in the storage volume.

It is preferred that the actuation mechanism and/or the drive portion comprise a ratchet mechanism. The ratchet mechanism may only allow and/or effect displacement of the insert in one direction along the displacement axis.

Preferably the actuation mechanism comprises at least one pawl and/or the drive portion comprises at least one rack of teeth. The pawl and the teeth form the ratchet mechanism. The pawl can also be termed a click. The pawl is advantageously arranged at the housing or connected to the housing, whereas the teeth are arranged at the insert. Particularly, the teeth can be arranged at an outer surface of the insert and can be arranged along the direction of the displacement axis.

Advantageously the actuation mechanism comprises a lever that is elastically bendable with respect to the housing, wherein the pawl is arranged at the lever. By operating the lever a force can be generated, whereby the pawl presses against the teeth and displaces the insert. Since the lever is elastically bendable, the lever can move back to its initial position after being released. When moving back to its initial position, the lever can also move the pawl "backwards", i.e. opposite the direction of displacement of the insert, wherein the pawl can then engage with the rack of teeth, again. The pawl can then displace the insert, again.

The lever can be forked, wherein one branch of the fork can comprise the pawl. The other branch can be configured as a gripping portion that allows the lever to be operated manually. The gripping portion may be formed at the end of the lever.

The lever can be hingedly attached at the housing, wherein the lever can pivot around the hinge. The pawl can be arranged closer to the hinge than an end of the lever without the hinge. In other words, the branch with the gripping portion may have a longer lever than the branch comprising the pawl. Thereby a force applied to the gripping portion can be amplified by the lever. A displacement of the insert and an ejection of a dose of component can then be facilitated without the need for excessive force.

Preferably the actuation mechanism can reach through a cut-out in a circumferential outer wall of the housing, when the actuation mechanism is operated, such that the actuation mechanism cooperates with the drive portion. The housing can have a substantially cylindrical outer contour.

Advantageously the lever may stick out from the housing. The housing may have a cutout for the rack of teeth of the insert. The pawl can then be arranged such that it reaches the teeth through the cutout.

Preferably the housing is made from a single material and is particularly formed as a single piece. Further, the levers and the housing can be formed integrally. In particular, the housing and/or the levers can be manufactured in an injection molding process.

More preferably the housing comprises a further pawl that is adapted to engage with the at least one rack of teeth. The further pawl may not be operated manually but be fixedly arranged at the housing. The further pawl can impede a backwards movement of the insert.

In this connection it should be noted that the further pawl may be arranged at a different rotational position with respect to the longitudinal axis compared to the pawl of the actuation mechanism. To allow the further pawl to engage with the at least one rack of teeth, the rack of teeth can preferably be arranged at the whole circumference or surface of the insert. The rack of teeth may therefore be at least partly circumferential to the insert. Alternatively the insert may comprise several racks of teeth, preferably four racks of teeth. An angle of 90° (if seen in the direction of the displacement axis) may be defined between two adjacent racks.

The applicator advantageously comprises a further actuation mechanism and a further drive portion, the further actuation mechanism and the further drive portion being preferably arranged opposite the actuation mechanism and the drive portion with respect to the displacement axis. In other words, the applicator may comprise at least two ratchet mechanisms. These ratchet mechanisms can be disposed symmetrically with respect to the displacement axis. Both ratchet mechanisms can be substantially identical or corresponding to each other. Generally, the actuation mechanism and the further actuation mechanism as well as the drive portion and the further drive portion may correspond to each other.

The applicator may therefore have two levers which allow easy operation with one hand, by pinching the two levers together. The two levers may stand off from the housing and therefore can appear to be wings that can be pinched together to eject one dose or drop of the flowable component.

Preferably, the housing and/or the insert comprise a substantially cylindrical shape. Such a cylindrical shape can easily be held in one hand, thereby further improving the handling of the applicator. The housing may be a hollow cylinder or a tube. The receiving portion may be the space inside the tube. Advantageously, the insert can also have a cylindrical form, wherein the outer diameter of the insert corresponds substantially to the inner diameter of the housing. A cylindrical housing and insert bear the advantage that the insert can be inserted in the housing independent of its rotational position with respect to the displacement axis. This additionally facilitates an easy handling of the applicator.

It is preferred that the storage volume is sealed with a pierceable material, particularly a pierceable film or foil. The storage volume can have a substantially cylindrical shape, wherein one base of the cylinder can be sealed with the pierceable material (the seal or sealing film). The cylinder surface can be the outer wall of the insert. The further base of the cylinder is made from a non-pierceable material.

A pierceable material is e.g. a material that can be penetrated with a sharp tip or edge. A sharp tip or edge may have a maximum dimension at its respective end of less than 1 mm. Even if penetrated, the pierceable material preferably will only get punctured at the site of piercing. This means, the pierceable material will advantageously not shatter or break at positions other than the position of the piercing. The pierceable material further advantageously has water and/or oxygen barrier properties.

The pierceable material can be formed by a flexible plastic, polymer and/or aluminum film. Further, the pierceable material can comprise polyolefin, cyclo-olefin-copolymer (COC), ethylene vinyl alcohol (EVOH), polyamide and/or polyester. Preferably the pierceable material is a multilayer film, e.g. comprising one layer of aluminum and one layer of polyolefin or cyclo-olefin-copolymer (COC). The thickness of the pierceable material can be in the range of 10 µm to 100 µm. Preferably the thickness is in the range of 30 µm to 70 µm. Advantageously the thickness is 50 µm.

Advantageously the housing comprises a piercing tip adapted to pierce the pierceable material, when the insert is displaced along the displacement axis. Upon a first displacement of the insert, the piercing tip "opens" the storage volume (by puncturing the pierceable material) thus allowing the ejection of the flowable component. The piercing tip and the application tip can be fluidly connected. Particularly, the piercing tip may comprise a fluid passage for the flowable component that can be formed as a central channel in the piercing tip.

After piercing of the seal of the storage volume the flowable component may then flow through the piercing tip to the application tip and can then be ejected from the application tip. Apart from the piercing necessary to allow a fluid connection, the piercing tip can be designed to seal the storage volume. Thereby a dripping of the flowable component can be prevented.

Preferably, the application tip can be made of or comprise a soft, flexible and/or porous material. The material of the application tip can reach into the fluid passage of the piercing tip.

Advantageously the piercing tip is adapted to displace the flowable component when the actuation mechanism is operated, wherein the piercing tip is stationary with respect to the housing. Furthermore, the piercing tip can move further and further inside the storage volume, each time the actuation mechanism is operated. The piercing tip can be integral with the housing.

To be more detailed, when the insert is displaced relative to the housing, the piercing tip preferably advances further inside the storage volume thereby reducing the volume of the storage volume. In other words, the piercing tip can act as piston or plunger for displacing the flowable component, in order to eject doses of the flowable component. The piercing tip can be adapted to displace the flowable component when the actuation mechanism is operated and/or to advance (with each operation of the actuation mechanism) further and further inside the storage volume, whereby the storage volume is reduced. The piercing tip preferably is in a fixed position relative to the further parts of the housing (i.e. the piercing tip is stationary with respect to the housing).

The piercing tip can be rotationally-symmetric around the displacement axis. The piercing tip can be surrounded by a cylindrical wall of the housing, wherein the wall of the housing has a spacing to the piercing tip.

It is advantageous, if an end region of the storage volume is adapted to the shape of the piercing tip. The storage volume can have a bullet-shape in a cross-sectional view. Due to the adapted shape of the piercing tip and the storage volume, the storage volume can be emptied almost completely, since the piercing tip can displace the flowable component nearly in its entirety.

The end region of the storage volume is defined by its proximal end, i.e. is the region of the storage volume that is emptied last, when the piercing tip advances further and further inside the storage volume.

The bullet-shape of the storage volume can at least partially be bordered by a sealing plane which may be formed by the pierceable material. The displacement axis may form a normal vector to the sealing plane. From the sealing plane the storage volume can extend towards its end region in the manner of a tube or a hollow cylinder. In its end region the storage volume forms a tip, i.e. the end region is adapted to the shape of the piercing tip. In a cross-sectional view an angle forming the tip of the storage volume can be smaller than 60°, preferably smaller than 45° or smaller than 30°. The tube or hollow cylinder can also extend from the sealing plane away from the end region, thus e.g. forming a cylindrical channel for the piercing tip. The cylindrical channel can lead the piercing tip to the sealing plane (i.e. the pierceable material). The piercing tip can also have a bullet-shape (the same shape as the storage volume).

Advantageously, the storage volume is formed by a container (or barrel), which is configured as a separate piece. In other words, the container is preferably not integral with the insert. The container can have the properties described above in connection with the storage volume. Particularly, an inner wall of the container can form the storage volume. An advantage of the separate container is that the container can be manufactured and filled with the flowable component independent from the (remaining) insert. The container can individually be placed into the insert before the insert is inserted into the housing, thus allowing to flexibly provide different inserts with different flowable components. The container can be fastened to the insert using a press fit and/or an adhesive bond. Particularly, the container can be slid inside the insert until an end of the container, particularly the end opposite the pierceable material, abuts against a stopping wall of the insert. The stopping wall can be parallel to the sealing plane. The container can be made of or comprise a plastic material and/or glass.

For example, the housing can have a substantially tubular shape. One end of the housing is terminated by the application tip. The end bordering the application tip is termed "distal", since in normal operation it is distal from the person using the applicator. Opposite the distal end, the housing comprises a proximal end having an opening in which the insert is introduced. After the insert is equipped with the container, the insert can be introduced into the housing.

It is preferable, if the applicator can be transitioned from a locked state to an unlocked state. The transition can be achieved by rotating the insert relative to the housing. In the locked state displacement of the insert relative to the housing along the displacement axis is substantially prevented and in the unlocked state displacement of the insert relative to the housing along the displacement axis is permitted. In the locked state displacement of the insert relative to the housing along the displacement axis can be prevented in both directions of the displacement axis. The applicator can thus comprise a safety function which prevents an unintentional ejection of the flowable component. To allow the ejection of the flowable component, a turning movement has to be applied to the insert of the applicator in order to unlock the applicator. The turning movement can be a rotation around the displacement axis.

In order to allow an easy gripping of the insert for the turning movement, the insert can comprise a grip portion. The grip portion is preferably arranged at an end of the insert.

The grip portion may stick out from the housing after the insert is initially received in the receiving portion of the housing. To unlock the applicator, the applicator may be held at the housing and at the grip portion of the insert thus allowing a twisting or a rotation of the insert relative to the housing. After the rotation of the insert the applicator is in the unlocked state and can be used to eject doses of the flowable component.

Preferably the rotation of the insert into the unlocked state leads to a displacement of the insert relative to the housing along the displacement axis, wherein the piercing tip pierces the pierceable material. The rotation of the insert thus not only unlocks the applicator but also leads to a defined movement of the insert along the displacement axis. The movement along the displacement axis causes the piercing tip to pierce e.g. the sealing film or foil of the storage volume. Thereby the handling of the applicator is further simplified since one movement, namely the rotation to unlock the applicator, also leads to the "opening" of the storage volume. This means that after the unlocking of the applicator, the first operation of the actuation mechanism will directly lead to the ejection of a first dose of the flowable component.

Advantageously, the insert comprises at least one retaining portion engaging the housing, whereby a removal of the insert from the housing is prevented, wherein the housing preferably comprises a guide slot for engaging with the retaining portion, the guide slot having a section being substantially circumferential to the displacement axis, and a longitudinal section being substantially parallel to the displacement axis. The retaining portion may have a wedged shape in order to allow a smooth inserting of the insert into the housing. To facilitate an easy insertion, the housing may additionally comprise at least one notch at an end opposite of the application tip. When the insert is inserted into the housing, the retaining portion can be guided by the notch. The notch can extend in the direction of the displacement axis.

After the insert has reached its initial position in the receiving portion, a withdrawal of the insert can be prevented as the retaining portion may be abutting against the guide slot. The guide slot and the retaining portion may further prevent the insert from being unintentionally inserted too deep into the housing, which would lead to the piercing of the sealing film and the uncontrollable ejection of the flowable component. This can be prevented by catching the retaining portion in the circumferential section of the guide slot.

Once the insert is inserted into the housing, due to the retaining portion the insert cannot be removed without the application of undue force. The applicator can therefore be a single-use applicator.

The circumferential section may span approximately 90° of the circumference of the housing. The circumferential section can have an angle of less than 90° with the displacement axis (when viewed in a projection to a plane comprising the displacement axis). The angle of less than 90° with the displacement axis can lead to a displacement of the insert along the displacement axis if the retaining portion is moved along the circumferential section. The retaining portion can be moved along the circumferential section if the insert is rotated relative to the housing, i.e. when the applicator is brought from the locked state into the unlocked state. The angle of smaller than 90° can thereby assure that the storage volume is opened by the piercing tip, when the applicator is brought into the unlocked state.

In the initial unlocked state the retaining portion can be positioned at a first end of the longitudinal section of the guide slot. Every operation of the actuation mechanism which leads to a displacement of the insert along the displacement axis also displaces the retaining portion along the displacement axis. This displacement leads to a movement of the retaining portion in the longitudinal section of the guide slot. The longitudinal section of the guide slot can be configured such that the retaining portion abuts against a second end of the longitudinal section when the flowable component is completely ejected.

Further advantageously a marker area (e.g. a colored area) is provided at the insert. Additionally the housing can comprise a cutout for the marker area, wherein more and more of the marker area can become visible as the insert advances into the housing. Particularly, the rack of teeth can be the marker area and is preferably provided with a color different from the remaining surface of the insert. The rack of teeth can become visible in the marker area upon ejection of doses of the flowable component. The cutout for the marker area may comprise or may be bordered by a click that engages with the rack of teeth and thereby prevents a backwards movement of the insert.

With respect to the displacement axis, the hinges of the levers can be arranged between the marker area and the guide slot.

Advantageously the storage volume is filled with the flowable component, the flowable component preferably being cyanoacrylate. The insert can thus be a cartridge comprising the flowable component.

Preferably the applicator described in the foregoing is used in the treatment of a patient, for example by applying or dispensing CA to the skin of a human. By applying CA to the skin, e.g. bed sores can be treated.

The invention further relates to a method of ejecting or dispensing doses of a flowable component, using an applicator of the kind described in the foregoing, the method comprising:

inserting an insert into a housing of an applicator,
operating an actuation mechanism to displace the insert relative to the housing along a displacement axis, thereby ejecting a dose of flowable component from a storage volume of the insert through an application tip.

Preferably, prior to operating the actuation mechanism, the insert and the housing are rotated relative to another in order to transition the applicator from a locked state into an unlocked state.

Advantageously operating the actuation mechanism is repeated a plurality of times to eject or dispense a plurality of doses of flowable component.

The invention also relates to an insert for an applicator of the kind described above. The insert comprises a drive portion for engaging with an actuation mechanism and a storage volume, the storage volume comprising a flowable component.

Additionally the invention also relates to a housing for an applicator of the kind described above. The housing comprises an actuation mechanism and a receiving portion for an insert. The actuation mechanism is configured to cooperate with a drive portion of the insert.

The housing and the insert can both be made by injection molding.

Furthermore, the invention relates to a kit of parts for ejecting doses of a flowable component, comprising a housing with an actuation mechanism and an insert with a drive portion. The insert is formed such that it can be inserted into a receiving portion of the housing. The insert can comprise a storage volume for or with the flowable component.

The advantages, preferable features and embodiments of the inventive applicator described in the foregoing also apply to the inventive method, the inventive insert, the inventive housing and the inventive kit of parts.

BRIEF DESCRIPTION OF THE DRAWINGS

The invention will be explained in more detail hereinafter with reference to the drawings.

DETAILED DESCRIPTION

Figure 1:
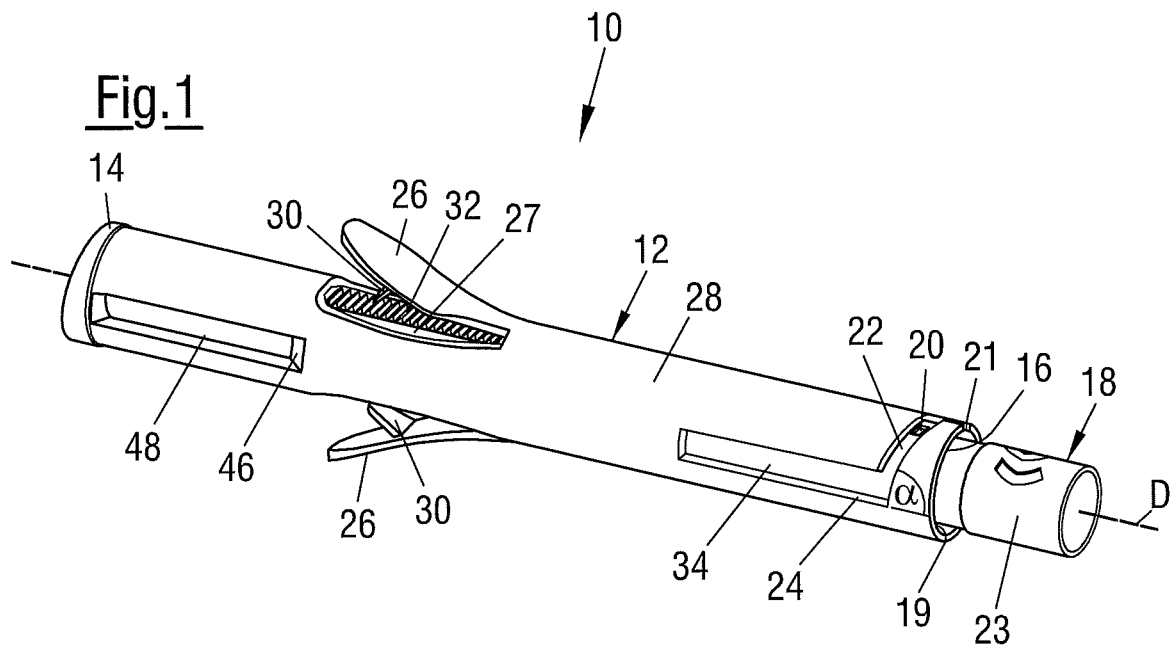
FIG. 1 is an applicator in a locked state.

In the following the same reference numerals will be used for parts having the same or equivalent function. Any statement made having regard to the direction of a component are made relative to the position shown in the drawing and can naturally vary in the actual position of application.

FIG. 1 shows a cylindrical applicator 10. The applicator 10 comprises a housing 12 that has a substantially tubular shape. One end of the housing 12 is terminated by an application tip 14. The end bordering the application tip 14 will in the following be termed "distal", since in normal operation it is distal from the person using the applicator 10. Opposite the distal end, the housing 12 comprises a proximal end having an opening 16 in which an insert 18 is introduced. Via the opening 16 the insert 18 is inserted into the tube-like inside of the housing 12, which can be considered a receiving portion 19 of the housing.

The insert 18 comprises a cylindrical shape and can be inserted into the housing 12 along a displacement axis D. The insert 18 comprises two retaining portions 20 arranged at opposite sides of the outer surface of the insert (only one is visible in FIG. 1). The retaining portions 20 are shaped wedge-like, i.e. they comprise a ramp that diminishes towards the distal end.

When the insert 18 is inserted into the housing 12 the retaining portions 20 first pass through two notches 21 and then snap into circumferential sections 22 of guide slots 24 (only one of the circumferential sections 22 and the guide slots 24 are visible in FIG. 1), wherein a further displacement of the insert along the displacement axis is prevented by the retaining portions 20 abutting against the borders of the circumferential sections 22.

The housing 12 comprises two levers 26 which are hingedly attached to an outer wall 28 of the housing. The levers 26 are made from a flexible material and further comprise two pawls 30.

In its normal position, each lever 26 sticks out from the housing 12, i.e. forms an angle of about 20° to 40° with the displacement axis D. The pawl 30 is inclined toward the displacement axis D and abuts against a rack of teeth 32 which is arranged at the outer surface of the insert 18.

The lever 26, the pawl 30 and the rack of teeth 32 form a ratchet mechanism.

The rack of teeth 32 is arranged circumferential at the outer surface of the insert 18. Alternatively, a plurality of racks can be provided at the insert 18.

Beneath each lever 26, a lever-cut-out 27 is provided in the outer surface of the housing. The lever-cut-out 27 allows the pawl 30 to engage with the rack of teeth 32.

FIG. 1 shows the applicator 10 in a locked position. A grip portion 23 of the insert 18 is outside the housing 12, if the applicator is in the locked state. As the retaining portions 20 are received in the circumferential sections 22 of the guide slots 24 a movement along the displacement axis D is substantially prohibited. Thus, even operation of the levers 26 would not move the insert 18 along the displacement axis D.

In order to transition the applicator 10 into an unlocked state, the insert 18 has to be rotated relative to the housing 12 such that the retaining portions 20 travel along the circumferential sections 22 until they reach two longitudinal sections 34 (only one is shown) of the guide slots 24.

The circumferential sections 22 each comprise an angle α of about 70° with the respective longitudinal section 34. Due to the angle α, the insert 18 is moved further inside the housing 12, when the insert 18 is rotated from the locked into the unlocked position.

Figure 2:
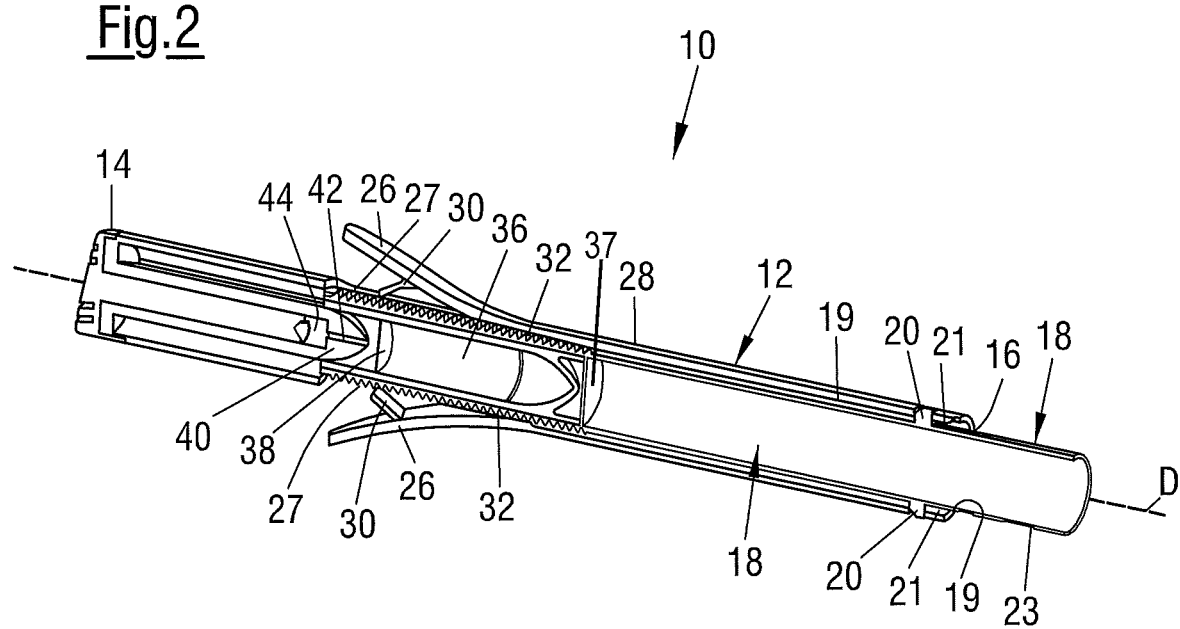
FIG. 2 is the applicator of FIG. 1 in a cross-sectional view.

FIG. 2 shows the applicator 10 in the locked position in a cross-sectional view such that the inside of the housing 12 and the insert 18 is visible.

Inside the insert 18 a container 36 for flowable component (e.g. a fluid, a gel or the like or a mixture such as a medical, dental, pharmaceutical, cosmetic, adhesive or veterinary preparation) is arranged at a distal end of the insert 18. The container 36 is fastened to the insert 18 by means of a press fit and abuts against a stopping wall 37. For the stopping wall 37 the displacement axis D forms a normal vector. At its distal end the container 36 is sealed by a sealing film 38 which is made from a pierceable material.

In the locked state, adjacent to the sealing film 38 a piercing tip 40 of the housing 12 extends into the inside of the insert 18. The piercing tip 40 has a bullet-like shape, as can be seen in greater detail in FIG. 5. At the center of the piercing tip an inlet to a central fluid channel 42 is provided. If flowable component flows from the container 36 through the fluid channel 42 it reaches a transmission volume 44 inside the piercing tip 40. The material of the application tip 14 extends into the transmission volume 44 such that the fluid component can enter the material of the application tip 14 in the transmission volume 44. The application tip 14 can be made from a soft or porous material.

Coming back to FIG. 2, it can be seen that the container 36 comprises the same bullet-like shape as the piercing tip 40 and is thereby adapted to receive the piercing tip 40.

Figure 3:
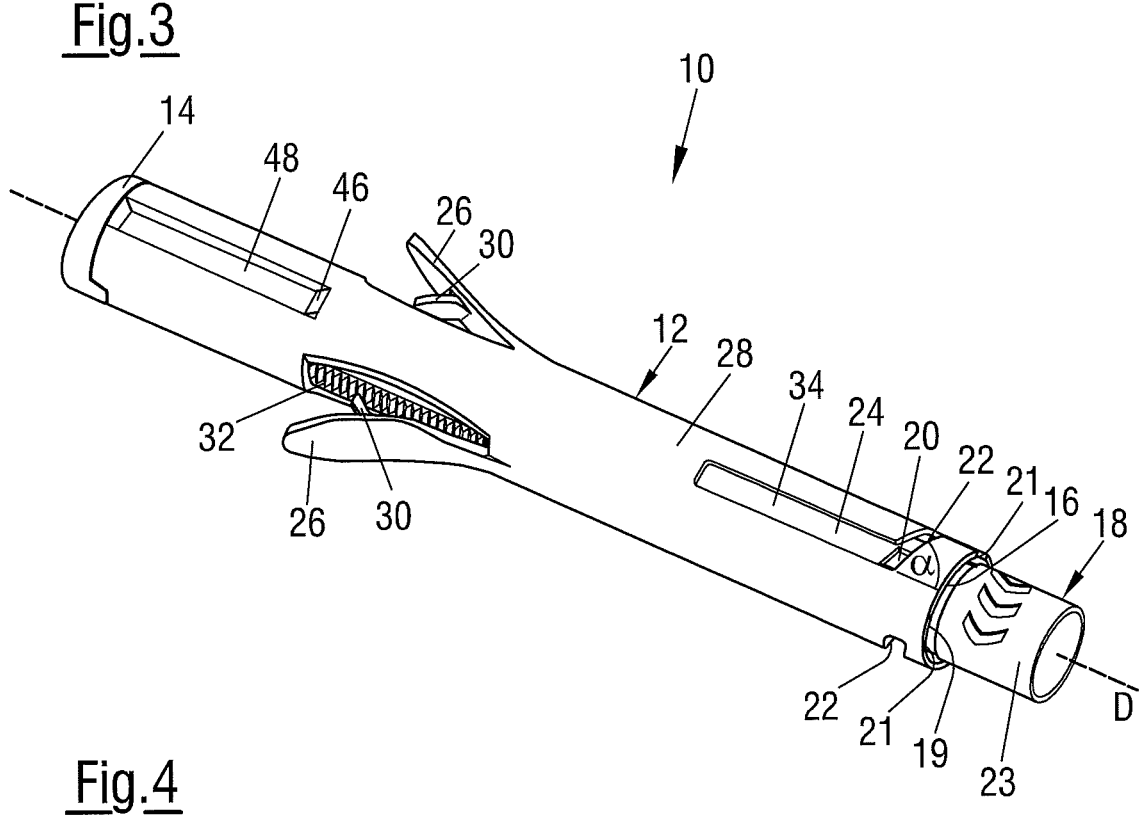
FIG. 3 is the applicator of FIG. 1 in an unlocked state.
Figure 4:
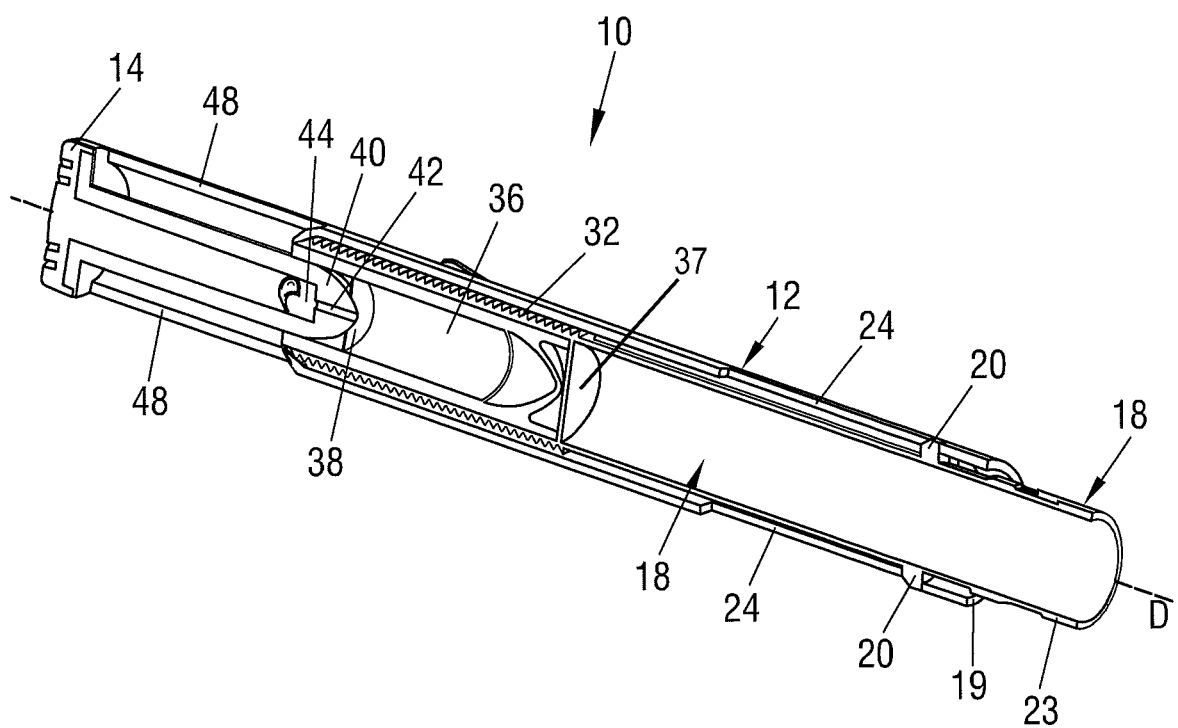
FIG. 4 is the applicator of FIG. 3 in a cross-sectional view.

Turning now to FIGS. 3 and 4 which show the applicator 10 in an initial unlocked state, wherein the retaining portion 20 is situated in the longitudinal section 34 of the guide slot 24. Compared to FIGS. 1 and 2, in FIGS. 3 and 4, the insert 18 has slightly advanced along the displacement axis D in the direction of the distal end of the applicator 10. Thereby, the piercing tip 40 pierced the sealing film 38 such that a fluid connection between the flowable component in the container 36 and the fluid channel 42 inside the piercing tip 40 is established.

In the unlocked state the levers 26 are operated, i.e. pinched toward the insert 18. Thereby, the pawls 30 engage with the rack of teeth 32 and advance the insert 18 further into the housing 12. In other words, the insert 18 is then displaced along the displacement axis D. Due to the displacement, the piercing tip 40 advances further inside the container 36 thereby reducing the volume of the container 36. Consequently, the flowable component stored inside the container 36 is then pressed through the fluid channel 42 and led to the application tip 14. Since every operation of the levers 26 displaces the insert 18 by approximately the same length along the displacement axis D, every operation of the levers 26 yields the same amount of flowable component that is ejected.

Figure 5:
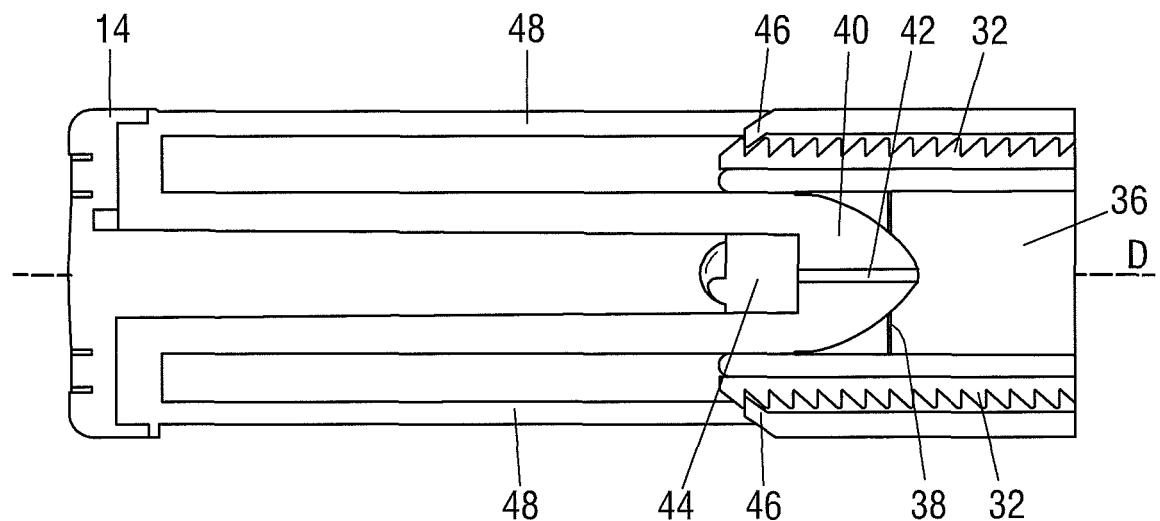
FIG. 5 is a detailed view of a piercing tip and an application tip.

When the insert 18 moves inside the housing 12, the rack of teeth 32 abuts against two clicks 46 that are shown in FIG. 5. The clicks 46 prevent a backwards movement of the insert 18. At the same time, when the insert 18 moves further inside the housing 12, the rack of teeth 32 becomes visible through an indicator cut out 48. The indicator cut out 48 provides a user with information about how much component is left in the container 36.

When the applicator 10 is operated, first the insert 18 is inserted into the housing 12. The retaining portions 20 are thereby caught in the circumferential sections 20 of the guide slots 24, i.e. the applicator 10 is in the locked state. The insert 18 is then rotated by approximately 90° relative to the housing 12 thus transitioning the applicator 10 into the unlocked state.

In the unlocked state the levers 26 are repeatedly pinched towards the insert 18, whereby the insert 18 is displaced in the direction of the distal end of the housing 12. The displacement is effected by the pawls 30 engaging with the rack of teeth 32. When the levers 26 are released, they return to their initial position, thereby moving the pawls 30 in the direction of the proximal end of the housing. After the levers 26 have returned to their initial position, the levers 26 can be operated in the same manner again until the container 36 is empty.

Figure 6:
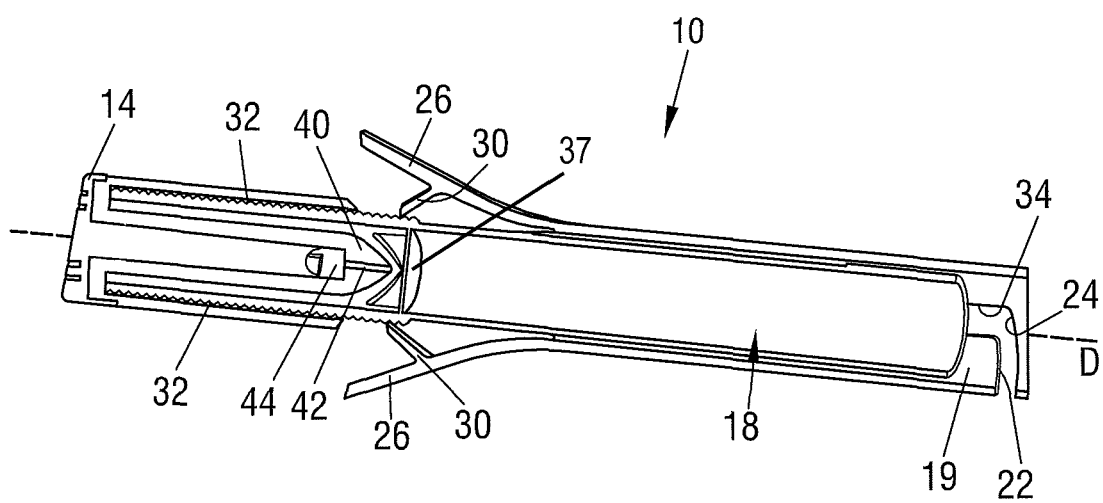
FIG. 6 is a cross-sectional view of an emptied applicator.

FIG. 6 shows the applicator 10 in an emptied state, i.e. the container 36 does not contain flowable component anymore but is fully filled with the piercing tip 40. In the emptied state the insert 18 abuts against the distal end of the housing 12.

The invention claimed is:

1. An applicator for ejecting doses of a flowable component, comprising:
    a housing;
    an application tip connected to the housing;
    an actuation mechanism; and
    an insert detachable from the housing, the insert being configured to be inserted into the housing, and having a storage volume for the flowable component, the storage volume sealed with a pierceable material,
    the housing including a receiving portion adapted to the insert,
    the insert including a drive portion configured to cooperate with the actuation mechanism so that the operation of the actuation mechanism results in a displacement of the insert relative to the housing along a displacement axis; and
    wherein the housing comprises a piercing tip configured to pierce the pierceable material, when the insert is displaced along the displacement axis.

2. The applicator of claim 1, wherein
    the applicator is configured such that at least two subsequent operations of the actuation mechanism result in displacements of the insert relative to the housing along the displacement axis.

3. The applicator of claim 1, wherein
    the actuation mechanism is integral with the housing.

4. The applicator of claim 1, wherein
    the actuation mechanism or the drive portion comprises a ratchet mechanism.

5. The applicator of claim 1, wherein
    the actuation mechanism is configured to reach through a cut-out in a circumferential outer wall of the housing, when the actuation mechanism is operated, such that the actuation mechanism cooperates with the drive portion.

6. The applicator of claim 1, further comprising
    a further actuation mechanism and a further drive portion, the further actuation mechanism and the further drive portion being arranged opposite the actuation mechanism and the drive portion with respect to the displacement axis.

7. The applicator of claim 1, wherein
    the piercing tip is configured to displace the flowable component when the actuation mechanism is operated, and the piercing tip is stationary with respect to the housing.

8. The applicator of claim 1, wherein
    the piercing tip is configured to move further inside the storage volume each time the actuation mechanism is operated, and the piercing tip is integral with the housing.

9. The applicator claim 1, wherein
    an end region of the storage volume is adapted to the form of the piercing tip.

10. The applicator of claim 1, wherein
    the storage volume has a bullet-shape in a cross-sectional view.

11. The applicator of claim 1, wherein
    the storage volume is defined by a container, which is configured as a separate piece.

12. The applicator of claim 1, wherein
    the applicator is capable of being transitioned from a locked state to an unlocked state by rotation of the insert relative to the housing, in the locked state displacement of the insert relative to the housing along the displacement axis is substantially prevented and in the unlocked state displacement of the insert relative to the housing along the displacement axis is permitted.

13. The applicator of claim 1, wherein
    the insert comprises a retaining portion engaging with the housing, whereby a removal of the insert from the housing is prevented, and
    the housing comprises a guide slot configured to engage the retaining portion, the guide slot having a circumferential section substantially circumferential to the displacement axis, and a longitudinal section substantially parallel to the displacement axis.

14. The applicator of claim 1, wherein
    the storage volume is filled with the flowable component, the flowable component being cyanoacrylate.

15. The insert for the applicator in accordance with claim 1, comprising:
    the drive portion configured to engage the actuation mechanism; and
    the storage volume comprising the flowable component.

16. A method of ejecting a flowable component, comprising:
    operating the applicator in accordance with claim 1, including
    inserting the insert into the housing of the applicator, and
    operating the actuation mechanism to displace the insert relative to the housing along the displacement axis, thereby ejecting a dose of flowable component from the storage volume of the insert through the application tip.

17. The applicator of claim 1, wherein
    the actuation mechanism comprises at least one pawl or the drive portion comprises at least one rack of teeth.

18. The applicator of claim 17, wherein
    the actuation mechanism comprises a lever elastically bendable with respect to the housing, and the pawl is arranged at the lever.

19. An applicator for ejecting doses of a flowable component, comprising:
    a housing;
    an application tip connected to the housing;

an actuation mechanism; and an insert detachable from the housing, the insert being configured to be inserted into the housing, and having a storage volume for the flowable component, the storage volume is defined by a container, which is configured as a separate piece and the container is fastened to the insert by a press fit or an adhesive bond, the housing including a receiving portion adapted to the insert, the insert including a drive portion configured to cooperate with the actuation mechanism so that the operation of the actuation mechanism results in a displacement of the insert relative to the housing along a displacement axis.

20. An applicator for ejecting doses of a flowable component, comprising:

a housing;

an application tip connected to the housing;

an actuation mechanism; and an insert detachable from the housing, the insert being configured to be inserted into the housing, and having a storage volume for the flowable component, the housing including a receiving portion adapted to the insert, the insert including a drive portion configured to cooperate with the actuation mechanism so that the operation of the actuation mechanism results in a displacement of the insert relative to the housing along a displacement axis, the applicator capable of being transitioned from a locked state to an unlocked state by rotation of the insert relative to the housing, in the locked state displacement of the insert relative to the housing along the displacement axis is substantially prevented and in the unlocked state displacement of the insert relative to the housing along the displacement axis is permitted, and rotation of the insert into the unlocked state leading to a displacement of the insert relative to the housing along the displacement axis, and a piercing tip pierces a pierceable material.

* * * * *